United States Patent [19]

Ser

[11] Patent Number: 5,603,939
[45] Date of Patent: Feb. 18, 1997

[54] FILM-FORMING COSMETIC COMPOSITION BASED ON A CHLORINATED GRAFT COPOLYMER RESULTING FROM THE GRAFTING OF A CHLORINATED POLYOLEFIN AND ACRYLIC, STYRENE AND/OR VINYL TYPE UNSATURATED MONOMERS

[75] Inventor: Jean-Claude Ser, Chevilly Larue, France

[73] Assignee: L'Oreal, Paris, France

[21] Appl. No.: 256,290

[22] PCT Filed: Nov. 12, 1993

[86] PCT No.: PCT/FR93/01110

§ 371 Date: Aug. 19, 1994

§ 102(e) Date: Aug. 19, 1994

[87] PCT Pub. No.: WO94/10966

PCT Pub. Date: May 26, 1994

[30] Foreign Application Priority Data

Nov. 12, 1992 [FR] France ................................ 92 13600

[51] Int. Cl.⁶ ...................................................... A61K 6/00
[52] U.S. Cl. .......................... 424/401; 424/450; 424/45; 424/59; 424/61; 524/460
[58] Field of Search ............................ 424/61, 45, 401, 424/59, 450; 524/460

[56] References Cited

U.S. PATENT DOCUMENTS

| | | | |
|---|---|---|---|
| 4,283,384 | 8/1981 | Jacquet et al. | 424/47 |
| 4,683,007 | 7/1987 | Horowitz et al. | 106/109 |
| 5,057,312 | 10/1991 | Langla et al. | 424/61 |
| 5,143,723 | 9/1992 | Calvo et al. | 424/61 |

FOREIGN PATENT DOCUMENTS

| | | |
|---|---|---|
| 0038004 | 10/1981 | European Pat. Off. . |
| 80/07328 | 10/1981 | France . |
| 81 03199 | 8/1982 | France . |
| 88 08172 | 12/1988 | France . |
| 2073229 | 10/1981 | United Kingdom . |
| 2207143 | 1/1989 | United Kingdom . |
| 2254082 | 9/1992 | United Kingdom . |

*Primary Examiner*—Mark D. Sweet
*Attorney, Agent, or Firm*—Oliff & Berridge

[57] ABSTRACT

Film-forming cosmetic composition containing, in a suitable cosmetic carrier, at least one grafted chlorinated copolymer resulting from the grafting of 5 to 20% of a chlorinated polyolefin with 80 to 95% of acrylic, styrene and/or vinyl type unsaturated monomers. Said monomers can be selected from oleophilic monomers taken alone or in mixture in a proportion of 0 to 95% and hydrophilic monomers taken alone or in mixture, in a proportion of 0 to 40%. The composition is useful in hair setting formulations or else in the preparation of nail varnish.

15 Claims, No Drawings

FILM-FORMING COSMETIC COMPOSITION BASED ON A CHLORINATED GRAFT COPOLYMER RESULTING FROM THE GRAFTING OF A CHLORINATED POLYOLEFIN AND ACRYLIC, STYRENE AND/OR VINYL TYPE UNSATURATED MONOMERS

The present invention relates to new film-forming cosmetic compositions containing, in a suitable vehicle, a chlorinated graft copolymer resulting from the grafting of a chlorinated polyolefin and acrylic, styrene and/or vinyl type unsaturated monomers.

Synthetic polymers and copolymers constitute essential ingredients of a large number of film-forming cosmetic compositions, such as hair fixing compositions, for example lacquers and setting lotions, or nail varnishes.

A very large number of polymers and copolymers have already been proposed, but few of them are capable of being used equally well in cosmetic compositions as different as hair-care products for fixing the hair and nail varnishes.

It has now been discovered that a certain class of copolymers resulting from the grafting of chlorinated polyolefins with unsaturated monomers yields cosmetic compositions of very diverse kinds, and that the latter bring about an improvement in the cosmetic properties, especially a better adhesion and sheen on keratinous substances such as eyelashes and hair, or alternatively on the nails.

It was established, more especially, that the adhesion of varnish was improved especially significantly by the use of such copolymers in nail varnishes.

The subject of the present invention is hence a film-forming cosmetic composition containing, in a suitable cosmetic vehicle, at least one chlorinated graft copolymer resulting from the grafting of 5 to 20% of a chlorinated polyolefin with 80 to 95% of acrylic, styrene and/or vinyl type unsaturated monomers, it being possible for the monomers to be chosen from oleophilic monomers, taken separately or mixed in a proportion of 0 to 95%, and hydrophilic monomers, also taken separately or mixed in a proportion of 0 to 40%.

According to the invention, the chlorinated polyolefins leading to the production of the chlorinated graft copolymer are characterized by an average molecular weight of between 8,000 and 140,000, and a chlorine content of between 15 and 40%.

Among unsaturated monomers, those of the oleophilic type are, more especially, styrene and alkyl, especially butyl, acrylates and methacrylates. Among unsaturated monomers of hydrophilic type, acrylic acid, methacrylic acid and 2-hydroxyethyl or 2-hydroxypropyl acrylates or methacrylates may be mentioned.

When the chlorinated graft copolymer is, more especially, intended for the production of a cosmetic composition in the form of nail varnish, the unsaturated monomers are of the oleophilic type, whereas when the chlorinated graft copolymer is intended for a hair-care cosmetic composition, the unsaturated monomers are of the hydrophilic type and more especially acrylic or methacrylic acid.

According to a preferred embodiment, the unsaturated monomers are in the form of a mixture consisting of styrene, butyl methacrylate, methacrylic acid and 2-hydroxyethyl methacrylate.

The chlorinated graft copolymers as defined above, present in the cosmetic compositions according to the invention, are obtained according to traditional polymer grafting processes, which consist in subjecting a chlorinated polyolefin dissolved in an organic solvent, for example xylene, to a grafting reaction using a suitable catalyst in the presence of at least one unsaturated monomer. After reaction has been allowed to proceed at the appropriate temperature, a secondary catalyst is optionally introduced, reaction is continued and the chlorinated graft copolymer is then isolated.

The grafting catalyst may be chosen, for example, from peroxides such as benzoyl peroxide, perbenzoates such as tert-butyl perbenzoate, hydroperoxides such as dicumyl hydroperoxide and diazo compounds such as 2,2'-azobis(isobutyronitrile) or 2,2'-azobis(2-methylbutyronitrile).

The secondary catalyst optionally used in the process is preferably chosen from dicumyl peroxide and di-tert-butyl peroxide.

The temperature of the grafting reaction is generally above 120° C., but preferably does not exceed 140° C.

The chlorinated graft copolymers obtained by the process as described above may be isolated or, preferably, may take the form of solutions with variable dry extracts which can be between 30 and 50%.

An example of preparation of a chlorinated graft copolymer will be given below as an illustration.

The cosmetic compositions according to the invention can take various forms, such as lotions, creams, emulsions, gels, solutions, milks, vesicular dispersions based on ionic or nonionic amphiphilic lipids, setting lotions or aerosol lacquers, or alternatively the form of nail varnish.

In the compositions according to the invention, the chlorinated graft copolymer may be present at a concentration of between 0.01 and 80% by weight, and preferably between 0.5 and 30% by weight, relative to the total weight of the composition.

These compositions can contain various cosmetic adjuvants such as fats, organic solvents, silicones, thickeners, emollients, UV-A or UV-B sunscreen agents, antifoams, hydrating agents, humectants, perfumes, preservatives, surfactants, fillers, sequestering agents, emulsifiers, anionic, nonionic and amphoteric polymers or mixtures thereof, alkalinizing agents, colorants, pigments, antioxidants, anti-free-radical agents and any other active agent customarily used in cosmetics.

As fats, special mention may be made of fatty acids, fatty alcohols, fatty acid esters such as $C_6$–$C_{18}$ fatty acid triglycerides, petroleum jelly, paraffin wax, lanolin and hydrogenated or acetylated lanolin.

Among oils, mineral, animal, vegetable or synthetic oils may be mentioned, and especially liquid paraffin, liquid petrolatum, caster oil, jojoba oil, sesame oil and also silicone oils and gums and isoparaffins.

Among animal, fossil, vegetable, mineral or synthetic waxes, beeswax, carob wax, candelilla wax, ozokerite, microcrystalline waxes and also silicone waxes and resins may be mentioned.

Among organic solvents, those preferably used in the cosmetic compositions according to the invention are $C_1$–$C_6$ lower monohydric alcohols or polyhydric alcohols such as ethanol, isopropanol, propylene glycol, glycerol, sorbitol, ketones such as acetone, esters such as butyl acetate or ethyl acetate and toluene.

As thickening agents, cellulose derivatives, crosslinked polyacrylic acid derivatives and guar or carob gums and also xanthan gum may be mentioned in particular. As thickening agents, organophilic clays, for example stearalkonium hectorite or bentone, may also be mentioned.

The cosmetic compositions according to the invention in the form of vesicular dispersions of ionic or nonionic amphiphilic lipids may be prepared according to standard processes such as are described, for example, in "Les Liposomes en Biologie Cellulaire et Pharmacologie" [Liposomes in Cell Biology and Pharmacology], Ed. INSERM, John Libbey, Eurotext, (1987), p.6–18.

According to an especially preferred embodiment of the invention, the cosmetic composition takes the form of a coloured or colourless nail varnish.

In this embodiment, the chlorinated graft copolymer is generally present in a proportion of between 0.5 and 45% by weight, and more especially between 5 and 25% by weight, relative to the total weight of the varnish.

As is well known, a traditional nail varnish is composed essentially of a solvent system, a film-forming substance, a resin and a plasticizing agent.

According to the invention, the film-forming substance consists of the chlorinated graft copolymer, used either alone or optionally mixed with a conventional film-forming substance such as nitrocelluloses.

The solvent system of the nail varnish consists essentially of a mixture of various volatile organic solvents, the purpose of this being to obtain relatively short drying times. The solvent system generally represents from 55 to 85% by weight of the total weight of the varnish.

Among these solvents, acetone, ethyl acetate, butyl acetate, 2-methoxyethyl acetate, methyl ethyl ketone, methyl isobutyl ketone, methyl acetate, amyl acetate and isopropyl acetate may be mentioned.

The solvent system can also comprise a diluent, which is preferably a saturated linear or branched hydrocarbon such as hexane or octane, or alternatively an aromatic hydrocarbon such as toluene or xylene, in a proportion generally of between 10 and 35% by weight relative to the total weight of the varnish.

The solvent system can also contain other volatile solvents, such as ethanol, n-butanol, n-propanol or isopropanol or mixtures thereof, as well as alkoxy alcohols such as methoxyethanol, ethoxyethanol and ethoxypropanol.

When the varnish according to the invention contains a secondary film-forming substance, appropriate compounds are, more especially, "RS" or "SS" type nitrocelluloses, especially nitrocellulose type ¼ second RS, nitrocellulose type ½ second SS and nitrocellulose type ⅝ second RS.

Other film-forming substances may optionally be used, for example polyvinyl derivatives such as polyvinyl butyrate as well as the copolymers described in French Patents Nos. 80/07328, 81/03199 and 88/08172.

In the nail varnishes according to the invention, the resin is generally present at a concentration of between 0.5 and 15% by weight relative to the total weight of the varnish.

Among the many resins which can be used, there may be mentioned, in particular, aryl sulphonamide/formaldehyde or arylsulphonamide/epoxy type resins, in particular the toluenesulphonamide/formaldehyde resin better known under the tradenames "Santolite MHP", "Santolite MS 80%" and "Ketjenflex MS 80", or alternatively alkyd resins such as those sold by the company Dainippon under the name "Beckosol Ode 230-70" and acrylic resins such as those sold by the the Company Rhom & Haas under the name "Acryloid B66".

The plasticizing agent of the nail varnish according to the invention is generally present at a concentration of between 2 and 10% by weight relative to the total weight of the varnish.

Especially preferred plasticizing agents according to the invention are preferably chosen from: tricresyl phosphate, benzyl benzoate, tributyl phosphate, butyl acetylricinoleate, glyceryl acetylricinoleate, dibutyl phthalate, butyl glycolate, dioctyl phthalate, butyl stearate, tributoxyethyl phosphate, triphenyl phosphate, triethyl citrate, tributyl citrate, tributyl acetylcitrate, tris(2-ethylhexyl) acetylcitrate, dibutyl tartrate, dimethoxyethyl phthalate, diisobutyl phthalate, diamyl phthalate, camphor, glyceryl triacetate and mixtures thereof.

When the nail varnish according to the invention takes a coloured form, it then contains at least one pigment of organic or inorganic nature.

Among organic pigments, D & C Red nos. 10, 11, 12 and 13, D & C Red no. 7, D & C Red nos. 5 and 6, D & C Red no. 34, lakes such as D & C Yellow no. 5 lake and D & C Red no. 2 lake and guanine may be mentioned.

Among inorganic pigments, titanium dioxide, bismuth oxychloride, brown iron oxide and red iron oxides may be mentioned, as well as synthetic pearlescenct agents such as titanium mica. These pigments can have undergone an inorganic or organic surface treatment, especially with a silicone or a polyethylene.

The pigments are generally present in the nail varnish in a proportion of between 0.01 and 2% by weight relative to the total weight of the varnish.

In order to avoid sedimentation of pigments, some thixotropic agents may be employed, such as, for example, "Bentone 27" or "Bentone 38". It is also possible to add rheology adjuvants to the varnishes, such as citric acid, phosphoric acid, para-toluenesulphonic acid or alternatively malic acid.

The nail varnishes according to the invention can also contain standard adjuvants such as, for example, UV screening agents, especially benzophenone or ethyl 2-cyano-3,3-diphenylacrylate, formaldehyde, vitamins such as vitamin E acetate and pantothenol, strengthening agents and antimycotics.

Some examples of preparation of chlorinated graft copolymers and also of cosmetic compositions containing them will now be given by way of illustration.

EXAMPLE OF PREPARATION OF CHLORINATED GRAFT COPOLYMERS

EXAMPLE 1

A solution of chlorinated polyethylene consisting of 1.34 kg of a 50% solution of chlorinated polyolefin in xylene, sold under the name "CP343" by the company Kodak (molecular weight: 18,000), and 0.48 kg of butyl acetate are introduced into a 20-litre reactor equipped with a stirrer and a device for purging with nitrogen. The temperature is brought to 135° C. under nitrogen, and a mixture of monomers consisting of 2.8 kg of styrene, 2.9 kg of butyl methacrylate, 1.16 kg of 2-hydroxyethyl methacrylate and 0.44 kg of methacrylic acid and the polymerization catalyst consisting of a mixture of 0.04 kg of azobis(isobutyronitrile) and 2.54 kg of butyl acetate are then added separately. The addition is carried out over 2 h 30 min, during which time the contents of the reactor are maintained at a temperature of 134°–135° C. The secondary catalyst consisting of 0.06 kg of tert-butyl peroxide and 4.7 kg of butyl acetate is then added over approximately one hour. Reaction is allowed to continue for 4 hours at 135° C., the mixture is then cooled to a temperature below 75° C. and the dilution solvent, namely 3.56 kg of ethyl acetate, is introduced. After cooling, a completely transparent viscous product which possesses the following characteristics is obtained:

| | |
|---|---|
| Dry extract at 90° C. | 43.8% |
| Transparency | Excellent |
| Content of residual monomers | 0.21% |

COMPOSITION EXAMPLES

EXAMPLE A: Nail varnish

| | |
|---|---|
| Chlorinated graft copolymer obtained according to Example 1 | 13% |
| Nitrocellulose | 4.9% |
| Isopropyl alcohol | 2.1% |
| Ethyl acetate | 13% |
| Butyl acetate | 49% |
| Formaldehyde (40% solution) | 0.4% |
| Acetyl tributyl citrate ("Citroflex A4" sold by the company Pfizer) | 7% |
| Camphor | 0.5% |
| Pigments | 0.1% |

The varnish obtained is shiny and has good retention.

EXAMPLE B: Nail varnish

| | |
|---|---|
| Chlorinated graft copolymer obtained according to Example 1 | 23% |
| Heptane | 10% |
| Ethyl acetate | 20% |
| Butyl acetate | 34.9% |
| Acetyl tributyl citrate ("Citroflex A4" sold by the company Pfizer) | 10% |
| DC Red 6 Ba lake | 0.3% |
| DC Red 7 Al lake | 0.2% |
| TiO$_2$ | 0.3% |
| Stearalkonium hectorite | 1.2% |
| Citric acid | 0.1% |

The varnish obtained is shiny and adheres well to the nail.

EXAMPLE C: Spray in pump bottle

| | |
|---|---|
| Chlorinated graft copolymer obtained according to Example 1 | 7% |
| 2-Amino-2-methyl-1-propanol | q.s. 100% neutralization |
| Perfume | q.s. |
| Ethanol | q.s. 100 g |

EXAMPLE D: Aerosol spray 40 g of the composition of Example C and then a propellent mixture consisting of:

| | |
|---|---|
| Dimethyl ether | 40 g |
| Pentane | 20 g | are introduced into an aerosol can.

After the can is closed, a suitable valve is fitted and the can is pressurized, an excellent spray giving a good power of fixing to the hair is obtained on spraying.

I claim:

1. A film forming cosmetic composition comprising, in a suitable cosmetic vehicle, an effective amount of a film forming chlorinated graft copolymer, said chlorinated graft copolymer consisting of 5 to 20% of a chlorinated polyolefin grafted with 80 to 95% of at least one member selected from the group consisting of an oleophilic monomer, a hydrophilic monomer and a mixture thereof; said oleophilic monomer being selected from the group consisting of styrene, alkyl acrylates, and alkyl methacrylates and said hydrophilic monomer being selected from the group consisting of acrylic acid, methacrylic acid, 2-hydroxyethyl acrylate, 2-hydroxyethyl methacrylate, 2-hydroxypropyl acrylate and 2-hydroxy-propyl methacrylate.

2. The cosmetic composition according to claim 1, wherein the chlorinated polyolefin is grafted with said mixture of oleophilic and hydrophilic monomers, said monomers being selected from the group consisting of styrene, butyl methacrylate, methacrylic acid and 2-hydroxyethyl methacrylate.

3. The cosmetic composition according to claim 1, wherein the chlorinated polyolefin has a chlorine content of between 15 and 40%.

4. The cosmetic composition according to claim 1, wherein the chlorinated graft copolymer is present at a concentration of between 0.01 and 80% by weight relative to the total weight of the composition.

5. The cosmetic composition according to claim 4, wherein the chlorinated graft copolymer is present at a concentration of between 0.5 and 30% by weight relative to the total of the composition.

6. The cosmetic composition according to claim 1, wherein said composition is in a form selected from the group consisting of a cream, an emulsion, a gel, a solution, a milk, a vesicular dispersion based on ionic or nonionic amphophilic lipid, a setting lotion and an aerosol lacquer.

7. The cosmetic composition according to claim 1, which further contains cosmetic ingredients selected from the group consisting of fats, organic solvents, silicones, thickeners, UV-A or UV-B sunscreen agents, humectants, perfumes, preservatives, surfactants, fillers, sequestering agents, emulsifiers, anionic, nonionic and amphoteric polymers or mixtures thereof, alkalinizing agents, colorants, pigments, antioxidants, and anti-free-radical agents.

8. A colored or colorless nail varnish comprising a solvent system consisting of a mixture of organic volatile solvents, a film-forming substance, an optional colorant, a resin and a plasticizing agent, said film-forming substance being a chlorinated graft copolymer consisting of 5 to 20% of a chlorinated polyolefin grafted with 80 to 95% of an oleophilic or hydrophilic monomer or a mixture thereof, said oleophilic monomer being selected from the group consisting of styrene, alkyl acrylates and alkyl methacrylates and said hydrophilic monomer being selected from the group consisting of acrylic acid, methacrylic acid, 2-hydroxyethyl acrylate, 2-hydroxyethyl methacrylate, 2-hydroxy propylacrylate and 2-hydroxypropyl methacrylate.

9. The nail varnish according to claim 8, wherein the chlorinated graft copolymer is present in a proportion of between 0.5 and 45% by weight relative to the total weight of the varnish.

10. The nail varnish according to claim 9, wherein the chlorinated graft copolymer is present at a concentration of between 5 and 25% by weight relative to the total of the varnish.

11. The nail varnish according to claims 8 and 10, characterized in that it contains nitrocellulose as secondary film-forming substance.

12. The nail varnish according to claim 8, which contains a resin selected from the group consisting of arylsulphonamide/formaldehyde or arylsulphonamide/epoxy resins, an alkyde resin and an acrylic resin, in a proportion of between 0.5 and 15% by weight relative to the total weight of the varnish.

13. The nail varnish according to claim 8, wherein the plasticizing agent is present in a concentration of between 2 and 10% by weight relative to the total weight of the varnish.

14. The nail varnish according to claim 8, which further contains at least one organic or inorganic pigment in a proportion of between 0.01 and 2% by weight relative to the total weight of the varnish.

15. The nail varnish according to claim 8, which further contains a nail varnish ingredient selected from the group consisting of UV screening agent, formaldehyde, vitamin E acetate, pantothenol, a strengthening agent and an antimycotic agent.

* * * * *